United States Patent
Baranski

(10) Patent No.: US 7,329,772 B2
(45) Date of Patent: Feb. 12, 2008

(54) METHOD FOR THE PREPARATION OF A HYDROXYALKYL HINDERED PHENOLIC ANTIOXIDANT

(75) Inventor: John R. Baranski, Southington, CT (US)

(73) Assignee: Crompton Corporation, Middlebury, CT (US)

( * ) Notice: Subject to any disclaimer, the term of this patent is extended or adjusted under 35 U.S.C. 154(b) by 644 days.

(21) Appl. No.: 10/835,046

(22) Filed: Apr. 29, 2004

(65) Prior Publication Data

US 2005/0242328 A1    Nov. 3, 2005

(51) Int. Cl.
C07C 67/02 (2006.01)
C07C 67/03 (2006.01)
C07C 67/48 (2006.01)
C09K 15/08 (2006.01)
C09K 15/32 (2006.01)

(52) U.S. Cl. ............. 560/75; 560/79; 560/92; 252/397; 252/400.61; 252/404; 508/198; 508/199; 508/200; 585/2; 554/7

(58) Field of Classification Search ........... 560/75; 252/400.61
See application file for complete search history.

(56) References Cited

U.S. PATENT DOCUMENTS

| | | | |
|---|---|---|---|
| 2,616,904 A | 11/1952 | Asseff et al. | 260/399 |
| 2,695,910 A | 11/1954 | Asseff et al. | 260/413 |
| 2,777,874 A | 1/1957 | Asseff et al. | 260/504 |
| 2,798,852 A | 7/1957 | Wiese et al. | 252/42.7 |
| 2,883,340 A | 4/1959 | Wasley et al. | 252/33 |
| 2,915,517 A | 12/1959 | Suer | 260/139 |
| 2,959,551 A | 11/1960 | Suer | 252/42.7 |
| 2,968,642 A | 1/1961 | Suer | 260/45.75 |
| 2,971,014 A | 2/1961 | Mastin | 260/398 |
| 2,989,463 A | 6/1961 | Mastin | 252/25 |
| 3,001,981 A | 9/1961 | Suer | 260/139 |
| 3,108,960 A | 10/1963 | Suer | 252/32.7 |
| 3,232,883 A | 2/1966 | Suer | 252/32.5 |
| 3,541,014 A | 11/1970 | Suer | 252/49.7 |
| 3,644,482 A * | 2/1972 | Dexter et al. | 560/75 |
| 3,657,322 A * | 4/1972 | Dexter et al. | 560/75 |
| 3,779,945 A | 12/1973 | Dexter et al. | 252/404 |
| 4,032,562 A | 6/1977 | Dexter et al. | 260/473 |
| 4,995,993 A | 2/1991 | Papke et al. | |
| 5,574,082 A * | 11/1996 | Keller et al. | 524/110 |
| 5,698,499 A * | 12/1997 | Baranski et al. | 508/198 |
| 6,448,208 B1* | 9/2002 | Dubs et al. | 508/229 |
| 2005/0230664 A1* | 10/2005 | Duyck et al. | 252/397 |

FOREIGN PATENT DOCUMENTS

| | | |
|---|---|---|
| WO | 94/22945 | 1/1994 |
| WO | WO03/051816 A1 | 6/2003 |

* cited by examiner

Primary Examiner—Joseph D. Anthony
(74) Attorney, Agent, or Firm—Katten Muchin Rosenman LLP

(57) ABSTRACT

A method of making a hindered phenolic antioxidant is disclosed wherein the method comprises:
reacting an ester of the formula:

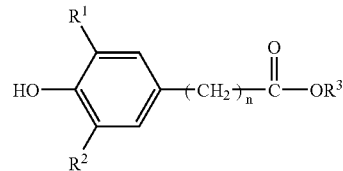

wherein
$R^1$, $R^2$, and $R^3$ are independently selected alkyl groups and n is 0, 1, or 2, with an aliphatic polyhydroxyl alcohol of the general formula $R(OH)_n$ wherein R is an aliphatic group of from 2 to about 12 carbon atoms and n is an integer of from 2 to 7, provided that one hydroxyl is primary and the others are secondary or tertiary, in the presence of a strong acid catalyst;
then, neutralizing the strong acid catalyst with an overbased detergent; and
isolating the hindered phenolic antioxidant after the neutralization step.

11 Claims, No Drawings

METHOD FOR THE PREPARATION OF A HYDROXYALKYL HINDERED PHENOLIC ANTIOXIDANT

BACKGROUND OF THE INVENTION

1. Field of the Invention

The present invention relates to a method for the preparation of materials that are useful as stabilizers for organic materials that are prone to deterioration via thermal and/or oxidative mechanisms. More particularly, the present invention relates to a method for the preparation of hindered phenolic antioxidants useful in stabilizing lubricants, especially lubricating oils, or other organic media.

2. Description of Related Art

Prior art methods for the stabilization of polyether polyols and other polymeric materials with antioxidants or other stabilizers and the use of the stabilized polyols in the preparation of polyurethane foams to inhibit scorch are well known. Polyether polyols, used in the manufacture of slabstock flexible and semi-flexible polyurethane foams, are typically stabilized with antioxidant packages comprising phenolic and amine antioxidants which may also contain synergists, such as phenothiazine or various compounds containing phosphite moieties.

WO 94/22945 discloses that organic materials that are subject to thermal and/or oxidative deterioration, e.g., polyether foams and polyurethane foams prepared from polyether polyols, can be stabilized against such deterioration by the addition thereto of a stabilizing amount of a liquid, crystallization-resistant mixture of phenolic esters made up predominantly of phenolic monoester(s), the mixture of phenolic esters being obtained by reacting an alkyl ester of a 3,5-dialkyl-4-hydroxyphenyl alkanoic acid with a polyhydroxyl alcohol under esterification reaction conditions employing an esterification reaction catalyst.

U.S. application Ser. No. 10/014,913, filed Dec. 14, 2001 discloses a method of preparing hindered phenolic antioxidants for lubrication oils or other organic media having reduced tin or titanium levels. A low amount of a tin or titanium catalyst is used resulting in low residual metal levels. The method provides for deactivation of the metal transesterification catalyst with an oxidizing agent, a reducing agent, or clay treatment. Treatment with clay, preferably acid treated clay, and more preferably acid treated bentonite clay, after deactivation with the oxidizing agent or reducing agent can further reduce residual tin levels to less than 10 ppm. By deactivating the metal catalyst prior to isolating the antioxidant from the reaction mixture, further reaction at the terminal diol of the reaction product is prevented. The final product mixture may be used without further purification and has improved solubility in lubrication oils and other organic media.

Oxidative stabilizers similar in structure and utility to the functionalized esters derived from (4-hydroxy-3,5-dialkylphenyl)alkanoic acids are disclosed in U.S. Pat. Nos. 3,644,482; 3,779,945; and 4,032,562. In U.S. Pat. No. 3,644,482, the alkanoic acid esters are terminated with aliphatic hydrocarbons. The compounds of U.S. Pat. No. 3,644,482 are isolated and crystallized.

U.S. Pat. No. 3,779,945 discloses stabilizer compositions containing mixtures of 3-(3,5-dialkyl-4-hydroxyphenyl)propionic acid esters of at least two non-identical alkanediols.

U.S. Pat. No. 4,032,562 discloses phenolic stabilizers, indicated for use in polymers such as polyurethanes, which are obtained by reacting a 3,5-dialkyl-4-hydroxyphenylalkanoic acid, acid chloride, or a lower alkyl ester with a saturated aliphatic glycol under known esterification conditions employing as catalyst a strong acid, such as para-toluene sulfonic acid.

The disclosures of the foregoing are incorporated herein by reference in their entirety.

SUMMARY OF THE INVENTION

The present invention is related to a process for the preparation of a hindered phenolic antioxidant for lubrication oils or other organic media. In a preferred embodiment, the product of the process is formed by reaction of, for example, methyl-(3,5-di-t-butyl(4-hydroxyphenyl))propionate and an aliphatic polyol, in which one hydroxyl group is primary and the other alcohol(s) is (are) hindered, i.e., secondary or tertiary. In the past, such products were made using catalysts, such as para-toluene sulfonic acid, that had to be washed out of the final product, producing extra reaction steps and much waste. Such washing steps to remove residual acid catalyst are necessary because:

1. Acid species cause corrosion. This is especially true under high temperature conditions, the conditions under which the antioxidant containing the acid catalyst would be used, as in a lubricant.
2. Acid species cause discoloration. The would be important where the antioxidant containing the acid catalyst were to be used as a polymer stabilizer, e.g., as in polyurethanes or polyethylenes/polypropylenes, where undesirable yellowing could result.
3. Acid species cause polymer property degradation.
4. Acid species are secondary catalysts in the formation of urethanes. This can cause abnormally high reaction temperatures leading to discoloration, physical property degradation, or combustion.

Other transesterification catalysts are available, such as dibutyl tin diacetate, but this material cannot be easily removed from the product, and where a vacuum stripping step is used to effect such removal, the live catalyst causes the formation of large amounts, e.g., 50-90 weight percent, of bis-product (the product formed when both hydroxyl groups of a diol react), which is generally considered less desirable that the mono-ester for the intended use.

A method has now been found that permits the preparation of a product in which the primary hydroxyl group of the aliphatic polyol selectively reacts to form the desired hydroxyl-terminated, i.e., mono-ester, species. This is accomplished by use of a strong acid catalyst, especially para-toluene sulfonic acid, followed by neutralization of the catalyst using an overbased detergent. Thus, the process of the present invention involves the neutralization of the catalyst by the overbased detergent before the vacuum stripping of excess aliphatic polyol. The reaction of the catalyst with the overbased detergent produces an insoluble solid that can be removed by filtration. Vacuum stripping of acid catalyzed product causes little or no change in it, i.e., the ratio of mono-ester to bis-ester remains substantially constant.

Benefits of the method of the present invention include substantial process cost savings (no washing steps) and much improved solubility of the product in mineral oils and formulated mineral oils.

More particularly, the present invention is directed to a method of making a hindered phenolic antioxidant comprising:

reacting an ester of the formula:

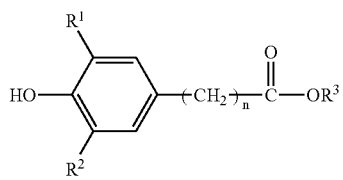

wherein $R^1$, $R^2$, and $R^3$ are independently selected alkyl groups and n is 0, 1, or 2, with an aliphatic polyhydroxyl alcohol of the general formula $R(OH)_n$ wherein R is an aliphatic group of from 2 to about 12 carbon atoms and n is an integer of from 2 to 7, provided that one hydroxyl is primary and the others are secondary or tertiary, in the presence of a strong acid catalyst;

then, neutralizing the strong acid catalyst with an overbased detergent; and isolating the hindered phenolic antioxidant after the neutralization step.

In a preferred embodiment, the present invention is directed to a process of making a hindered phenolic antioxidant comprising:

providing an ester of the formula:

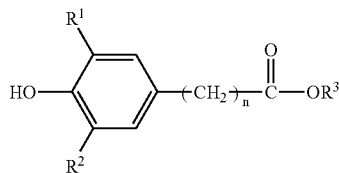

wherein $R^1$, $R^2$, and $R^3$ are independently selected alkyl groups and n is 0, 1, or 2;

providing an aliphatic polyhydroxyl alcohol of the general formula $R(OH)_n$, wherein R is an aliphatic group of from 2 to about 12 carbon atoms and n is an integer of from 2 to 7, provided that one hydroxyl is primary and the others are secondary or tertiary;

providing a strong acid catalyst;

heating the ester and the aliphatic polyhydroxyl alcohol in the presence of the strong acid catalyst to react the primary hydroxyl group of the aliphatic polyhydroxyl alcohol with the ester to transesterify said ester to form a product mixture comprising a mono-ester;

neutralizing the strong acid catalyst with an overbased detergent; and isolating the hindered phenolic antioxidant after the neutralization step.

Preferably, the mono-ester product of the process will have the structure:

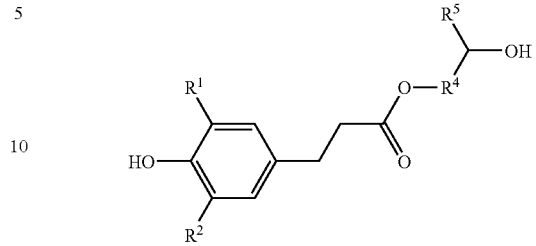

wherein:

$R^1$ and $R^2$ are independently selected from the group consisting of branched alkyl moieties of from 3 to 6 carbon atoms, $R^4$ is an alkylene moiety of from 1 to 6 carbon atoms, and $R^5$ is an alkyl group of from 1 to 6 carbon atoms, or a hydroxyl-substituted alkyl group of from 1 to 6 carbon atoms.

DESCRIPTION OF THE PREFERRED EMBODIMENTS

The stabilizer compositions that are prepared by the process of the present invention are obtained by reacting at least one alkyl ester of a 3,5-dialkyl-4-hydroxyphenyl alkanoic acid with at least one polyhydroxy alcohol under esterification reaction conditions employing an esterification catalyst.

The starting alkyl esters of 3,5-dialkyl-4-hydroxyphenyl alkanoic acid are preferably selected from among those of the general formula:

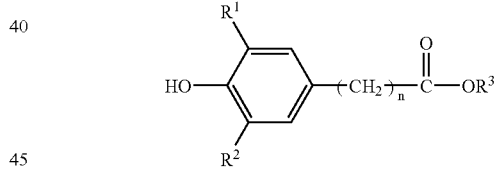

wherein $R^1$, $R^2$, and $R^3$ are the same or different and each represents an alkyl group, preferably of from 1 to 6 carbon atoms, and n is 0, 1, or 2. Such alkyl groups include methyl, ethyl, propyl, butyl, pentyl, hexyl, and the like, and isomers thereof. Preferred starting phenolic esters include those in which $R^1$ and/or $R^2$ are relatively bulky groups, such as t-amyl, t-butyl, and the like. The compounds methyl 3-(3,5-di-t-butyl-4-hydroxyphenyl)propionate, ethyl 3-(3,5-di-t-butyl-4-hydroxyphenyl)propionate, and propyl 3-(3,5-di-t-butyl-4-hydroxyphenyl)propionate are especially preferred; methyl 3-(3,5-di-t-butyl-4-hydroxyphenyl)propionate is most preferred.

The starting polyhydroxyl alcohols are preferably selected from among the aliphatic polyhydroxyl alcohols of the general formula $R(OH)_n$ wherein R is an aliphatic group of from 2 to about 12 carbon atoms and n is an integer of from 2 to 7. Representative of the preferred group of aliphatic polyhydroxyl alcohols are such compounds as ethylene glycol, the propanediols, the butanediols, the pentanediols, the hexanediols, the heptanediols, the octanediols, glycerol, trimethylol propane, pentaerythritol, and the like, and combinations of any of the foregoing, provided that one hydroxyl is primary and the others are secondary or tertiary. Preferably, the aliphatic polyhydroxy alcohol is selected from the group consisting of ethylene glycol, 1,2-propane diol, 1,3-propane diol, 1,2-butane diol, 1,3-butane diol, 1,4-butane diol, 2,3-butane diol, 1,2-pentane diol, 1,3-pentane diol, 1,4-pentane diol, 1,5-pentane diol, 2,3-pentane diol, 2,4-pentane diol, 1,2-hexane diol, 1,3-hexane diol, 1,4-hexane diol, 1,5-hexane diol, 1,6-hexane diol, 2,3-hexane diol, 2,4-hexane diol, 2,5-hexane diol, glycerol, trimethylol propane, and pentaerythritol. Diols possessing a secondary hydroxyl group, such as 1,2-propanediol and 1,3-butanediol, and triols such as glycerol, are especially preferred for use herein. Such alcohols tend to provide mixtures of phenolic esters having greater resistance to crystallization.

While the mole ratio of polyhydroxyl alcohol to phenolic ester reactant can be less than, equal to, or greater than 1, it is generally desirable to use a molar excess of the alcohol, as this is likely to increase the amount of phenolic monoester(s) in the reaction product. In general, the mole ratio of polyhydroxyl alcohol to phenolic ester can preferably vary from about 1.2:1 to about 10:1, more preferably from about 1.5:1 to about 6:1 and most preferably from about 1.7:1 to about 4:1.

Suitable reaction temperatures can range from about 100° to about 190° C., preferably from about 120° to about 175° C.

Other reaction conditions that may affect the outcome of the reaction and the nature of the product mixture include the type of esterification catalyst used. It is known in the art that, although both basic and acidic esterification catalysts could be used, it is preferred to employ an acidic catalyst, such as p-toluene sulfonic acid, especially when the polyhydroxyl alcohol reactant contains a secondary hydroxyl group, so as to provide reaction mixtures of the greatest complexity, in turn providing mixtures of phenolic esters having the greatest crystallization resistance. The esterification catalyst is generally employed at from about 0.1 to about 10, and preferably from about 0.5 to about 2.0, mole percent of the starting phenolic ester. The reaction time will ordinarily be on the order of from about four to about five hours. Other acidic catalysts that can employed include, but are not limited to, sulfuric acid; hydrochloric acid; Lewis acids, such as boron trifluoride, tin and zinc salts, aluminum halides, and organic-titanates; other sulfonic acids, such as benzenesulfonic acid or methanesulfonic acid; phosphoric acid; and the like.

Monitored by gas chromatographic methods, the reaction can be allowed to continue until the phenolic ester reactant remaining possesses an area percent of less than about 5%, preferably less than about 2% and more preferably less than about 1%.

In the practice of the present invention, the acidic catalyst is neutralized after the esterification reaction with an overbased Group II metal-containing detergent. These complexes are a well-known class of basic metal-containing compositions that have generally been employed as detergents and dispersants in lubricating oil compositions. See, for example, U.S. Pat. No. 3,541,014 and other art referred to therein. These "overbased" complexes are also referred to in the art as "superbased" or "hyperbased" complexes or salts, basic complexes, basic metal complexes, "high-metal containing" salts and complexes, basic complex salts, and the like.

Overbased materials are characterized by a metal content in excess of that which would be present according to the stoichiometry of the metal and the particular organic compound said to be overbased. Thus, if an oil-soluble monosulfonic acid is neutralized with a basic metal compound, e.g., calcium hydroxide, the "normal" metal salt produced will contain one equivalent of calcium for each equivalent of acid. However, various known procedures are available that produce oil-soluble products containing more than the stoichiometric amount of metal. These oil-soluble products are the overbased materials employed to neutralize the acidic catalysts in the process of the present invention.

Applying these known procedures, an oil-soluble sulfonic acid or an alkali or alkaline earth metal salt thereof can be reacted with a Group II metal base and the product will contain an amount of metal in excess of that required to neutralize the sulfonic acid, for example, 4.5 times as much metal as would be present in the normal salt, or a metal excess of 3.5 equivalents. The actual stoichiometric excess of metal can vary considerably, for example, from about 0.1 equivalent to about 30 or more equivalents depending on the reactions, the process conditions, and the like.

The term "overbased" is used herein to designate materials containing a stoichiometric excess of metal and is, therefore, inclusive of those materials which have been referred to in the art as overbased, superbased, hyperbased, etc., as mentioned above.

Generally, these overbased materials are prepared by treating a reaction mixture comprising (a) the organic compound to be overbased, (b) a reaction medium consisting essentially of at least one substantially inert, organic solvent for said organic material, (c) a stoichiometric excess of a metal base, and (d) a promoter with an acidic material. The methods for preparing the over-based products and an extremely diverse group of overbased products are well known in the prior art and are disclosed, for example, in a number of U.S. patents, such as those referred to in U.S. Pat. No. 3,541,014, the disclosure of which is incorporated herein by reference.

Organic compounds that can be overbased are generally oil-soluble compounds characterized by an essentially hydrocarbon portion containing at least about 12 aliphatic carbon atoms or at least about 8 aliphatic carbon atoms and one or more aromatic hydrocarbon rings and a polar portion such as an acid group. The hydrocarbon portion can contain polar substituents so long as the hydrophilic character thereof is not destroyed. The hydrocarbon portion can contain up to 250 or more carbon atoms, but generally will contain not more than about 60 carbon atoms.

Suitable acids include oil-soluble organic acids, such as phosphorus acids, thiophosphorus acids, sulfur acids, carboxylic acids, thiocarboxylic acids, and the like, as well as the corresponding alkali and alkaline earth metal salts thereof. Overbased acids wherein the acid is a phosphorus acid, a thiophosphorus acid, phosphorus acid-sulfur acid combination, or sulfur acid prepared from polyolefins are disclosed in U.S. Pat. Nos. 2,883,340; 2,915,517; 3,001,981; 3,108,960; and 3,232,883. Overbased phenates are disclosed in U.S. Pat. No. 2,959,551 while overbased ketones can be found in U.S. Pat. No. 2,798,852.

A variety of overbased products prepared from oil-soluble metal-free, non-tautomeric neutral and basic organic polar compounds, such as esters, amines, amides, alcohols, ethers, sulfides, sulfoxides, and the like are disclosed, for example, in U.S. Pat. Nos. 2,968,642; 2,971,014; and 2,989,463.

The metal compounds used in preparing the overbased products are normally the basic salts of metals in Group II of the Periodic Table. The anionic portion of the salt can be hydroxyl, oxide, carbonate, hydrogen carbonate, nitrate, sulfite, hydrogen sulfite, halide, amide, sulfate, etc. as disclosed in the above-cited patents. The overbased products are preferably prepared from the alkaline earth metal oxides, hydroxides, and alcoholates. The alkaline earth metal lower alkoxides are the preferred alcoholates.

Promoters, that is, materials that facilitate the incorporation of the excess metal into the overbased product are also quite diverse and well known in the art. A particularly comprehensive discussion of suitable promoters is found in U.S. Pat. Nos. 2,777,874; 2,695,910; and 2,616,904. These include alcoholic and phenolic promoters, which are preferred. Water is used in combination with the promoters in some instances to increase their effectiveness.

It should be apparent that the overbased products may retain all or a portion of the promoter. That is, if the promoter is not volatile (e.g., an alkyl phenol) or otherwise readily removable from the overbased material, at least some promoter may remain in the overbased product. The presence or absence of the promoter in the overbased material used to neutralize the acidic catalyst does not represent a critical aspect of the present invention. Clearly, it is within the skill of the art to select a volatile promoter, such as a lower alkanol, e.g., methanol, ethanol, and the like, so that the promoter can be readily removed prior to the neutralization, if desired.

The overbased products are preferably prepared using inorganic acidic materials, such as HCl, $SO_2$, $SO_3$, $CO_2$, $H_2S$, $N_2O_3$, and the like. The overbased products prepared with $CO_2$ are particularly suitable. Materials capable of producing the acidic reactants in situ may also be used. For example, urea, carbamates, and ammonium carbonates produce $CO_2$ in situ.

In preparing the overbased products, the compound to be overbased, a substantially inert organic solvent therefor, the metal base, the promoter, and the acidic material are brought together and a chemical reaction ensues. The exact nature of the resulting overbased product is not known. However, it can be adequately described for purposes of the present specification as a single phase homogeneous solution of a Group II metal-containing complex formed from the metal base, the acidic material, and the compound being overbased.

A typical preparation of an overbased product would involve mixing a phenolic promoter, a Group II metal base, and the organic compound to be overbased and treating the mixture with carbon dioxide at a temperature of at least about 50° C., preferably from 80° C. to 250° C. The upper temperature limit is determined by the decomposition point of the reaction mixture. The carbonation is preferably carried out in the presence of a fluid diluent, usually an organic solvent in which the organic compound to be overbased and the product is soluble. Solvents commonly useful for this purpose are substantially inert organic solvents such as benzene, toluene, chlorobenzene, naphtha, dodecane, xylene, mineral oil, and combinations thereof.

The relative amounts of the compound to be overbased and the metal base are such that at least 1.1 equivalents of the metal base is normally used per equivalent of the compound to be overbased. There appears to be no upper limit on the amount of the metal base that may be used in the process. For practical reasons, however, the amount of the metal base seldom exceeds 25 equivalents per equivalent of the compound being overbased. A greater amount of the metal compound may be used, but there appears to be no particular advantage attending such use. Usually, from about 2 to about 15 equivalents of the metal base is used.

The equivalent weight of a given organic compound which is to be overbased depends upon the number of functional groups in the molecule and the equivalent weight of the metal compound depends upon the valence of the metal and the number of the metal radicals in the molecule. For example, the equivalent weight of a phenol is determined by the number of hydroxy radicals attached to the aromatic nucleus.

When the reaction mixture is contacted with the acidic material, either in the presence of or in the absence of a diluent, it is usually a heterogeneous mixture. As acidification (e.g., carbonation) proceeds, the metal base becomes solubilized in the organic phase and the carbonated product eventually becomes a homogeneous composition that is readily soluble in hydrocarbon solvents, such as benzene, xylene, or mineral oil. It is not necessary in most instances that all of the metal base present in the process mixture should be so converted in order to produce a soluble homogeneous product. Such a product is often obtained, for example, when as little as 75% of the metal base is carbonated.

The advantages and the important features of the present invention will be more apparent from the following examples.

EXAMPLES

Naugard® PS-40, an antioxidant that is commercially available from Crompton Corp. of Middlebury, Conn., is a complex mixture of species, prepared by transesterification of 1,3-butane diol and methyl-(3,5-di-t-butyl-(4-hydroxyphenyl))propionate. The transesterification products are comprised primarily of one ("mono") or two ("di") equivalents of methyl-(3,5-di-t-butyl-(4-hydroxyphenyl))propionate and numerous ether-containing condensation side-products.

The original process for the preparation of this antioxidant used an acid catalyst, para-toluene sulfonic acid (p-TSA), and employed five water washes to remove the catalyst. The water washing process was chosen because it gave a product of very low color, an important characteristic for the intended use of the antioxidant in the polymer stabilizer market; however, the multiple water washes and final vacuum distillation rendered product prepared by the original process too expensive for use in other applications, in particular, lubricant additives.

In accordance with the present invention, an economical process was found that utilized an overbased calcium sulfonate detergent as a neutralization agent for the acid catalyst. The calcium carbonate in the detergent reacts with the acid catalyst to form carbon dioxide and a solid calcium salt. Filtration of the product and then vacuum distillation yielded the final product.

Example 1

Comparative Example

This example illustrates the preparation of alkylhydroxy (3,5-di-t-butyl{4-hydroxyphenyl}propionate for use in the product of this invention and the removal of the catalyst by bicarbonate neutralization and water extraction of neutralization products. (Reference Example 1 in U.S. Pat. No. 5,698,499.) This is the standard preparation procedure of the prior art. Here, sodium bicarbonate is used to neutralize the acid and the by-products are extracted by water washes.

A five-liter, four-neck, round-bottom flask was equipped with an overhead stirrer, a subsurface nitrogen sparge tube, a thermocouple probe, and a Graham condenser. The Graham condenser was fitted with a simple distillation head and a condenser. The vessel was charged with 1,880 grams of methyl 3-(3,5-di-t-butyl-4-hydroxyphenyl)propionate; 3,090 milliliters of 1,3-butanediol; and 12.8 grams of p-toluene sulfonic acid monohydrate. The mole ratio of 1,3-butane diol to phenolic ester reactant was about 5.4:1.

The system was purged with nitrogen, agitated, and warmed to 145° C. The system was held at 145° C. for 5.5 hours. The reaction mass was allowed to cool to about 80° C. and, thereafter, 750 milliliters of an Ashland Chemical Co. product of an aliphatic petroleum naphtha sold under the designation Lacolene were added. The solution was initially extracted with 800 milliliters of 0.12 M sodium bicarbonate and then extracted three times with 200 milliliter portions of water. Any remaining volatile matter was removed by rotary evaporation. The yield of light-colored, liquid product was 1,957 grams. The product obtained was a complex mixture of phenolic esters having a moderate viscosity at room temperature.

GC Results: No detectable p-toluene sulfonic acid.

Example 2

In this Example, the overbased detergent/filtration procedure to neutralize and remove the catalyst and by-products is illustrated. The preparation of alkylhydroxy(3,5-di-t-butyl{4-hydroxyphenyl}propionate for use in the product of this invention and the removal of the catalyst by overbased detergent neutralization and filtration of neutralization salts is illustrated.

Methyl 3-(3,5-di-t-butyl-4-hydroxyphenyl)propionate (2.66 mol), 1,3-butane diol (5.32 mol), and p-toluene sulfonic acid (0.031 mol) were combined in a 2-liter reaction flask equipped with an overhead stirrer, thermocouple, nitrogen inlet and a distillation condenser. The reaction was run at 145° C. for 6 hours. Upon completion of the reaction, a sample was taken for gas chromatography analysis and then the catalyst was neutralized with HITEC 611, an overbased calcium sulfonate detergent with a TBN (total base number) of 300. The resulting product was opaque due to the calcium salt by-product. Vacuum distillation at 120° C. and 29 inches of mercury for one hour and then pressure filtration using 5 wt % diatomaceous earth filter aide and a one-micron filter yielded a clear, straw-yellow product.

GC analysis showed no appreciable change in the mono/di ratio of the final product.

GC Results: No detectable p-toluene sulfonic acid.

Example 3

This example illustrates the preparation of alkylhydroxy (3,5-di-t-butyl{4-hydroxyphenyl}propionate for use in the product of this invention. No attempt was made to neutralize or remove the catalyst from this product.

Methyl 3-(3,5-di-t-butyl-4-hydroxyphenyl)propionate (0.266 mol), 1,3-butane diol (0.532 mol) and p-toluene sulfonic acid (00.031 mol) were combined in a 250 mL reaction flask equipped with an overhead stirrer, thermocouple, nitrogen inlet, and a distillation condenser. The reaction was run at 145° C. for 8 hours. The excess diol was removed at 120° C. and 29 inches of mercury vacuum for 8 hours. The final product was a straw-colored medium viscosity liquid.

This example shows the effect of no neutralization on the catalyst level in the final product. This was the only sample with detectable levels of catalyst. The fact that there is not much present is due to its volatilizing off during the exaggerated (8 hour) vacuum strip. The strip step was exaggerated in an attempt to force production of more bis-product, which was unsuccessful.

GC Results: Sample contained 0.05 relative area percent p-toluene sulfonic acid.

TABLE 1

| Example | Catalyst Neutralization Method | Residual Catalyst* |
|---|---|---|
| 1 | p-TSA, Bicarbonate and water washes | None detected |
| 2 | p-TSA, Detergent neutralization | None detected |
| 3 | p-TSA, None | 0.05 RA % |

*Residual catalyst level was determined by gas chromatography.

In view of the many changes and modifications that can be made without departing from principles underlying the invention, reference should be made to the appended claims for an understanding of the scope of the protection to be afforded to the invention.

What is claimed is:

1. A method of making a hindered phenolic antioxidant comprising:

reacting an ester of the formula:

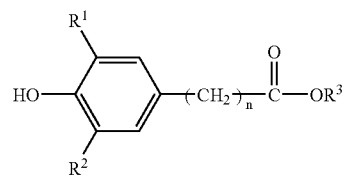

wherein $R^1$, $R^2$, and $R^3$ are independently selected alkyl groups and n is 0, 1, or 2, with an aliphatic polyhydroxyl alcohol of the general formula $R(OH)_n$ wherein R is an aliphatic group of from 2 to about 12 carbon atoms and n is an integer of from 2 to 7, provided that one hydroxyl is primary and the others are secondary or tertiary, in the presence of a strong acid catalyst;

then, neutralizing the strong acid catalyst with an overbased detergent; and isolating the hindered phenolic antioxidant after the neutralization step.

2. A method of making a hindered phenolic antioxidant comprising:

providing an ester of the formula:

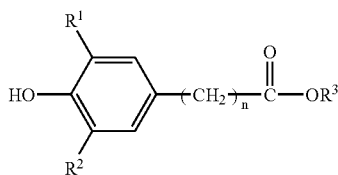

wherein
R¹, R², and R³ are independently selected alkyl groups and n is 0, 1, or 2;
providing an aliphatic polyhydroxyl alcohol of the general formula R(OH)$_n$ wherein R is an aliphatic group of from 2 to about 12 carbon atoms and n is an integer of from 2 to 7, provided that one hydroxyl is primary and the others are secondary or tertiary;
providing a strong acid catalyst;
heating the ester and the aliphatic polyhydroxyl alcohol in the presence of the strong acid catalyst to react the primary hydroxyl group of the aliphatic polyhydroxyl alcohol with the ester to transesterify said ester to form a product mixture comprising a mono-ester;
neutralizing the strong acid catalyst with an overbased detergent; and
isolating the hindered phenolic antioxidant after the neutralization step.

3. The method of claim 2 wherein the aliphatic polyhydroxyl alcohol is selected from the group consisting of ethylene glycol, 1,2-propane diol, 1,3-propane diol, 1,2-butane diol, 1,3-butane diol, 1,4-butane diol, 2,3-butane diol, 1,2-pentane diol, 1,3-pentane diol, 1,4-pentane diol, 1,5-pentane diol, 2,3-pentane diol, 2,4-pentane diol, 1,2-hexane diol, 1,3-hexane diol, 1,4-hexane diol, 1,5-hexane diol, 1,6-hexane diol, 2,3-hexane diol, 2,4-hexane diol, 2,5-hexane diol, glycerol, trimethylol propane, and pentaerythritol.

4. The method of claim 2 wherein the aliphatic polyhydroxyl alcohol is employed at a level in excess of the stoichiometric amount required for reaction with the ester.

5. The method of claim 4 further including the step of removing any residual aliphatic polyhydroxyl alcohol after the step of neutralizing the strong acid catalyst.

6. The method of claim 2 wherein the aliphatic polyhydroxyl alcohol is 1,3-butane diol.

7. The method of claim 2 wherein the strong acid catalyst is para-toluene sulfonic acid.

8. The method of claim 2 wherein the overbased detergent is an overbased calcium sulfonate detergent.

9. The method of claim 2 wherein R¹ and R² are both tert-butyl, n is 2, and R³ is methyl.

10. A method of making making a hindered hydroxyalkyl phenolic antioxidant comprising the steps of:
reacting methyl-(3,5-di-t-butyl(4-hydroxyphenyl)) propionate with a stoichiometric excess of 1,3-butanediol in the presence of a para-toluene sulfonic acid catalyst;
neutralizing the para-toluene sulfonic acid catalyst with an overbased detergent; and
removing any residual aliphatic polyhydroxyl alcohol after the neutralization step to isolate the product mixture.

11. The method of claim 10 wherein the overbased detergent is an overbased calcium sulfonate detergent.

* * * * *